(12) United States Patent
McKinney et al.

(10) Patent No.: US 8,875,702 B2
(45) Date of Patent: Nov. 4, 2014

(54) AEROSOL GENERATOR

(75) Inventors: Walter McKinney, Morgantown, WV (US); Dave Frazer, Fairmont, WV (US); Bean Chen, Morgantown, WV (US)

(73) Assignee: The United States of America as represented by the Secretary of the Department of Health and Human Services, Centers for Disease Control and Prevention, Washington, DC (US)

( * ) Notice: Subject to any disclaimer, the term of this patent is extended or adjusted under 35 U.S.C. 154(b) by 325 days.

(21) Appl. No.: 12/871,453

(22) Filed: Aug. 30, 2010

(65) Prior Publication Data

US 2011/0108023 A1 May 12, 2011

Related U.S. Application Data

(60) Provisional application No. 61/237,945, filed on Aug. 28, 2009.

(51) Int. Cl.
*A61M 15/00* (2006.01)
*A61M 11/00* (2006.01)
*A61M 16/16* (2006.01)

(52) U.S. Cl.
CPC ......... *A61M 11/005* (2013.01); *A61M 15/0086* (2013.01); *A61M 2205/3368* (2013.01); *A61M 16/16* (2013.01); *A61M 2205/3331* (2013.01); *A61M 2205/07* (2013.01); *A61M 11/001* (2013.01); *A61M 16/161* (2013.01)
USPC ................................................... 128/203.15

(58) Field of Classification Search
CPC ................. A61M 15/0085; A61M 2016/0021; A61M 15/0065; A61M 17/0646; A61M 11/005; A61M 15/0045; A61M 2202/064
USPC ............ 128/200.16, 200.21, 200.22, 203.24, 128/203.25, 203.27; 239/4, 102.1, 102.2; 222/39, 226, 232, 234, 241, 243, 249, 222/278, 282, 284, 270, 275
See application file for complete search history.

(56) References Cited

U.S. PATENT DOCUMENTS 2,840,417 A * 6/1958 Dorsak et al. ................. 239/335
3,318,308 A * 5/1967 Grosholz ................. 128/204.15
(Continued)

FOREIGN PATENT DOCUMENTS

EP 20070022472 A1 5/2008
WO WO-03017015 A1 2/2003
(Continued)

OTHER PUBLICATIONS

Austin et al, Design and use of an inhalation chamber for air pollution studies in small animals, Journal of the South African Veterinary Association, 1978, 235-238, 49(3).
(Continued)

*Primary Examiner* — Melanie Hand
*Assistant Examiner* — Ned T Heffner
(74) *Attorney, Agent, or Firm* — Gifford, Krass, Sprinkle, Anderson & Citkowski, P.C.; Weston R. Gould

(57) ABSTRACT

A sonic aerosol generator is provided that provides a constant concentration of particulate aerosol over a long exposure time to an animal. The concentration of aerosols is maintainable for greater than 30 hours at concentrations of 15 mg/m$^3$ or more. The aerosol generator is used to expose subject to high concentrations of aerosols that more accurately represents the levels that may be seen in a workplace environment.

25 Claims, 14 Drawing Sheets

(56) References Cited

U.S. PATENT DOCUMENTS

| | | | |
|---|---|---|---|
| 3,387,607 A * | 6/1968 | Gauthier et al. | 128/200.16 |
| 3,669,108 A * | 6/1972 | Sundblom et al. | 128/204.26 |
| 3,861,386 A * | 1/1975 | Harris et al. | 128/200.16 |
| 4,333,450 A * | 6/1982 | Lester | 128/200.14 |
| 4,961,885 A * | 10/1990 | Avrahami et al. | 261/142 |
| 5,388,574 A | 2/1995 | Ingebrethsen | |
| 5,887,586 A * | 3/1999 | Dahlback et al. | 128/204.22 |
| 6,601,581 B1 * | 8/2003 | Babaev | 128/200.16 |
| 6,814,317 B2 * | 11/2004 | Watanabe et al. | 239/602 |
| 7,290,542 B1 * | 11/2007 | Carpin | 128/200.21 |
| 2009/0025714 A1 | 1/2009 | Denyer et al. | |

FOREIGN PATENT DOCUMENTS

| | | |
|---|---|---|
| WO | WO-2004017848 A1 | 3/2004 |
| WO | WO-2004022243 A1 | 3/2004 |
| WO | WO-2007015803 A2 | 2/2007 |

OTHER PUBLICATIONS

Baron et al, Aerosolozation of single-walled carbon nanotubes for an inhalation study, Inhalation toxicology , 2008, 751-760, 20(8).

Chakravarty et al, Thermal ablation of tumor cells with antibody-functionalized single-walled carbon nanotubes, PNAS, Jun. 24, 2008, 8697-8702, 105(25).

Han et al, Monitoring Multiwalled Carbon Nanotube Exposure in Carbon Nanotube Research Facility, Inhalation Toxicilogy, 2008, 741-749, 20.

Liu et al, in vivo biodistribution and highly efficient tumor targeting of carbon nanotubes in mice, Nature Nanotechnology, 2006, 47-52, 2.

Maynard et al, Exposure to carbon nanotube material: aerosol release during the handling of unrefined single-walled carbon nanotube material, Journal of Toxicology and Environmental Health, 2004, 87-107, Part A, 67.

Maynard et al, Airborne nanostructured particles and occupational health, Journal of Nanoparticle Research, 2005, 587-614, 7.

McKinney et al, Computer controlled ozone inhalation exposure system, Inhalation Toxicology, 2008, 43-48, vol. 20 Issue 1.

Mitchell et al, Pulmonary and systemic immune response to inhaled multiwalled carbon nanotubes, Toxicological Sciences, 203-214, 2007, 203-214, 1000(1).

Oberdörster et al, Principles for characterizing the potential human health effects from exposure to nanomaterials: elements of a screening strategy, Particle and Fibre Toxicology, 2005, 2:8.

Oberdörster et al, Nanotoxicology: An Emerging discipline evolving from studies of ultrafine particles, Environmental Health Perspectives, Jul. 2005, 823-839, 113(7).

Phalen, 1976, Inhalation exposure of animals, Environmental Health Perspectives, 17-24, vol. 16.

Wong, 2007, Inhalation exposure systems: design, methods and operation, Toxicology Pathology 35:3.

* cited by examiner

AEROSOL GENERATOR

CROSS REFERENCE TO RELATED APPLICATIONS

This application claims priority to U.S. Provisional Application No. 61/237,945 filed Aug. 28, 2009, the entire contents of which are incorporated herein by reference.

FIELD OF THE INVENTION

An apparatus and method are provided for generating aerosols and delivery of aerosols to an organism. An aerosol generator acoustically produces uniform and well controlled particulate aerosols. The resulting aerosols are delivered to an organism through a real time monitored delivery apparatus such that exposure levels are instantly tunable and regulatable for long time periods.

BACKGROUND OF THE INVENTION

Nanotechnology involves the synthesis of nanostructures having at least one dimension and a size between 1 and 100 nanometers. These nanostructures are regularly applied in the manufacturing of medical products, drug delivery systems, consumer goods, and miniature electrical components. Carbon nanotubes are of particular interest for the production of nanostructures in that the carbon provides exceptional thermal and electrical conductivity properties allowing their potential use in chemical sensors and catalysts. Some nanotubes have been used in medicine to deliver therapeutic agents to the brain (Oberdorster, et al., 2004) and tumors (Liu et al., 2006. Chakravarty, et al., 2008).

Multi-walled carbon nanotubes (MWCNT) offer excellent potential for industrial and medical uses. Prior to the application of these materials, however, there is a need to improve the understanding of their adverse toxicological effects on workers involved in the production and use of these products. Exposure to nano-sized particles during the manufacture, handling and cleanup of engineered nanomaterials may present extreme hazards to workers depending on the physical and chemical characteristics of the materials that may produce different biological responses than larger materials of the same chemical composition. (Maynard et al., 2004; Oberdorster et al., 2005; Oberdorster, et al, 2005). Low-solubility nanoparticles are more toxic than larger particles of the same material on an equal mass basis (Orberdorster, et al., 2005) illustrating the importance of performing toxicological investigations of manufactured nano-sized particles prior to worker exposure.

Several methods for aerosolizing carbon nanotubes to evaluate their health effects in animals have been described. Mitchell et al. employed a system including a screw feeder, jet mill, and cut-point cyclone to produce a respirable aerosol. (Mitchell et al., 2007) This system produced low concentrations of nanotubes of between 0.1 and 1 mg/m$^3$. The Mitchell method separates fibers by injecting them into a turbulent air stream where they undergo high velocity collisions with other carbon nanotubes similar to the processes used to pulverize materials such as silica. The energy associated with this separation process may alter the physical properties of the aerosolized carbon fibers compared with those found in the air of a carbon nanotube production facility. Care must be taken when extending results generated using this system to actual worker exposure.

A second method employs an ultra high speed knife mill to chop single walled carbon nanotubes to form small particles (Baron et al. 2008). The Baron system produces aerosols that can be used for inhalation studies, although it generates considerable noise that may cause additional stresses to the animals in the exposure chamber. This method also requires continuous adjustments by a well-trained technician.

Due to the importance in obtaining meaningful data relating to the biological effects of MWCNT, and other particulate or molecule containing aerosols, there exists a need for an apparatus and method of delivering highly controlled aerosols of particulate matter for meaningful experimental time periods to an organism.

SUMMARY OF THE INVENTION

An aerosol generator is provided that includes an acoustic energy generator acoustically coupled to a first side of a first diaphragm having a first side and a second side. The first diaphragm is physically coupled to an aerosol chamber.

The atmospheric pressure on the first side or the second side of the first diaphragm is tunable. The atmospheric pressure on the second side of the first diaphragm is optionally higher than the atmospheric pressure on the first side of the diaphragm. In some embodiments the atmospheric pressure on the second side of the first diaphragm is from −0.3 to 0.5 inch-H$_2$O different than pressure on the first side of the first diaphragm, optionally 0.1 inch-H$_2$O higher than the atmospheric pressure on the first side of the first diaphragm.

An exposure chamber is optionally atmospherically coupled to the aerosol generator.

The aerosol produced by an aerosol generator optionally has a concentration of 0.1 to 15 mg/m$^3$, optionally from 5 to 12 mg/m$^3$, optionally any range or value therebetween. The concentration of the aerosol is optionally held constant for 30 hours or less using 5 grams of substrate material. In some embodiments the concentration of the aerosol is optionally held to a concentration within 20 percent of target or average concentration for at least 1 hour, optionally from 1 to 25 hours.

The first diaphragm has a focal zone that is optionally in excess of 2 centimeters.

The acoustic generator optionally generates acoustic energy of sinusoidally oscillating frequency that optionally is variable above and below a resonant frequency of the first diaphragm, the aerosol chamber, or the combined aerosol chamber and first diaphragm.

In some embodiments a computer is electrically connected to at least one portion of said aerosol generator whereby the computer is programmed to maintain a concentration of aerosol to within 20 percent or less an average or target aerosol concentration for at least 1 hour, optionally for 1 to 25 hours or any range or value therebetween.

A process of exposing a subject to an aerosol is also provided wherein a subject is placed in an exposure chamber that is atmospherically coupled to an aerosol generator such as that described herein, and exposing the subject to an aerosol produced by the generator at an aerosol concentration from 0.1 to 15 mg/m$^3$ for an exposure time of at least 1 hour. During the exposure time, the aerosol in the exposure chamber is maintained to a concentration of within 20 percent an average or target concentration. The process is optionally performed in an exposure chamber that includes a nephelometer electrically coupled to a computer, wherein the computer maintains a constant aerosol concentration in response to signal from said nephelometer.

A process of generating an aerosol is also provided including placing an aerosol source on an acoustic energy translating surface, and exposing the energy translating surface to an oscillating acoustic energy. The process optionally includes separating aerosol particles by elutriation. The acoustic energy is optionally oscillated above and below a resonant frequency of the acoustic energy translating surface alone or coupled to an aerosol chamber. The oscillating acoustic energy is optionally unfocused.

Acoustic energy is optionally provided in the process at less than 1000 Hz, optionally, less than 40 Hz.

A substrate material used in the processes is optionally multi-walled carbon nanotubes. It is appreciated that multiple substrates are optionally used to generate a heterogeneous aerosol.

DESCRIPTION OF THE PREFERRED EMBODIMENTS

The inventions described herein and their equivalents have utility as an aerosol generator and method of delivering aerosol to a subject. An aerosol generator is provided that is optionally incorporated into an exposure system capable of exposing subjects to constant concentrations of aerosols such as aerosols of multi-walled carbon nanotubes. The aerosol exposure system optionally meets the following specific requirements: 1) an aerosol generator produces airborne particles continuously for long periods of exposure time (5 or more hours), 2) the physical characteristics of the aerosolized particles, illustratively multi-walled carbon nanotubes, mimic aerosols found in the workplace, 3) the exposure concentration is maintained automatically by the system with minimal fluctuations during an exposure period, 4) the size distribution of the airborne exposure particles remains constant during consecutive exposure periods, 5) the exposure concentration response time is minimal after subjects have been placed into the exposure chamber, 6) the overshoot in exposure concentration during the initial rise transient is minimal, 7) the system is optionally computer controlled and requires little to no operator intervention over the exposure period.

Figure 1:
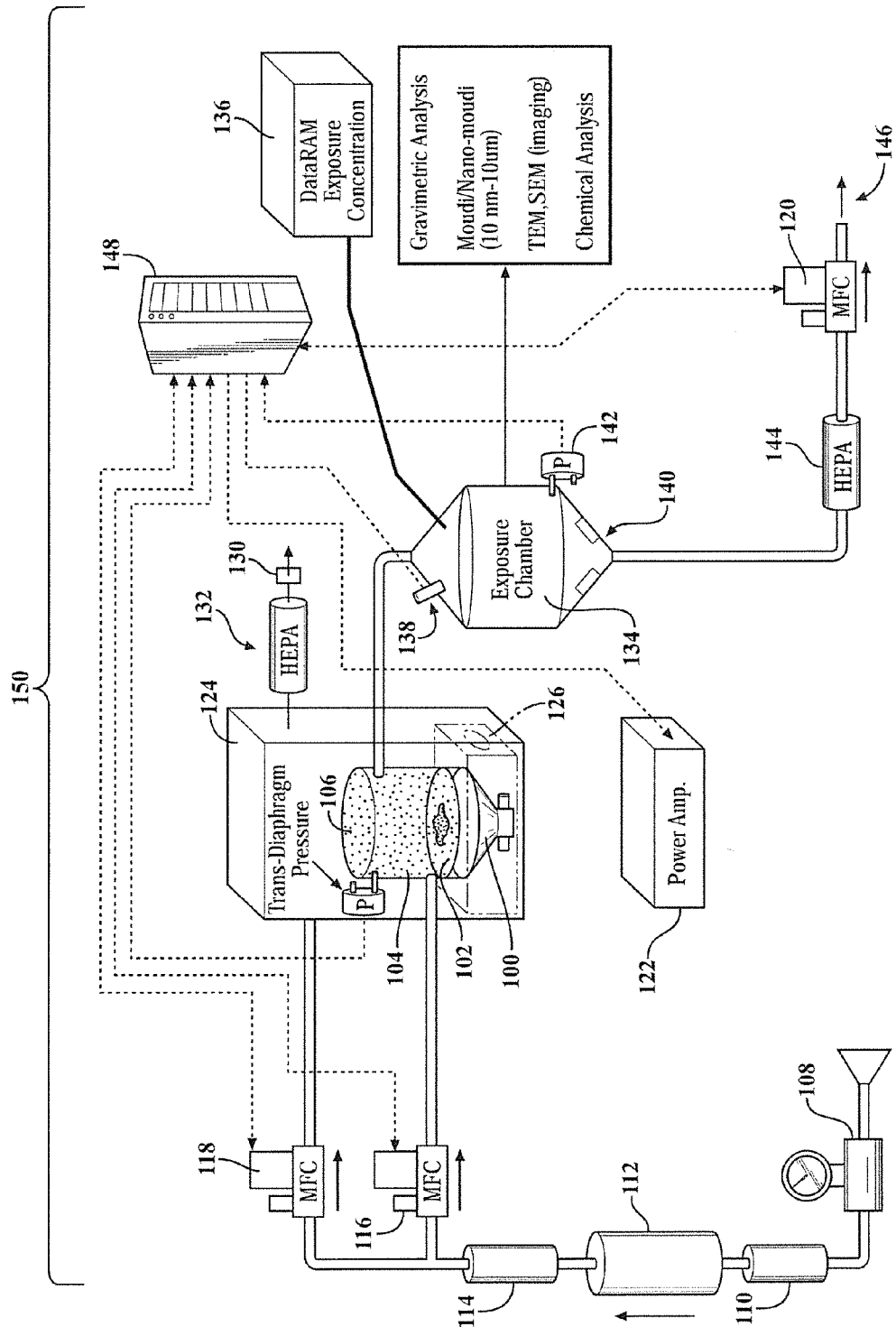
FIG. 1 is a schematic of a combination aerosol generator and an exposure chamber according to one embodiment of the invention for exposing a subject to one or more aerosols.

An aerosol generator is provided whereby aerosols generated by the aerosol generator are optionally transferred to an optionally associated exposure chamber that provides for examination of the affects of aerosol exposure on a subject. Referring to FIG. 1, an aerosol generator includes an acoustic energy generator 100 acoustically coupled to an acoustic energy translating surface. An acoustic energy translating surface is illustratively a diaphragm. The acoustic energy generator is optionally acoustically coupled to a first diaphragm 102. A first diaphragm includes a first side and a second side. Acoustic energy from the acoustic energy generator 100 is transferred through the first diaphragm 102 to the second side of the first diaphragm. The first diaphragm is coupled to an aerosol chamber 104 where acoustic vibrations transferred through the first diaphragm are translated to a substrate material causing generation of aerosols in the aerosol chamber 104. An aerosol generator is capable of tuning the atmospheric pressure on the first side and/or the second side of the first diaphragm 102.

An acoustic energy generator is optionally any acoustic loudspeaker operable for generating acoustic energy of the desired frequency and amplitude. An illustrative example is a subwoofer such as that available from Ciare (Italy). It is appreciated that loudspeakers from other sources are similarly operable. A loudspeaker is optionally electrically coupled via a wire or other coupling to an amplifier that powers the acoustic energy generator 100 and allows a user to adjust the frequency of the acoustic energy generated from the acoustic energy generator 100 either manually, automatically, or both.

The frequency of acoustic energy produced by an acoustic energy generator is optionally constant or variable. In some embodiments the acoustic energy is of a sinusoidally oscillating frequency. A sinusoidally oscillating frequency optionally has a frequency range that varies above and below the resonant frequency of the first diaphragm and aerosol chamber combination or either a first diaphragm or aerosol chamber alone. This resonance frequency is primarily a combination of the dimensions of the aerosol chamber and the one or more diaphragms and is easily determinable by one of ordinary skill in the art. Acoustic energy optionally varies from 5 to 1000 Hz or any subdivision therebetween, optionally from 10 to 20 Hz. In some embodiments the acoustic energy has a frequency of 40 Hz or less, optionally 20 Hz or less. Acoustic energy optionally varies with a period from 1 to 60 seconds or any subdivision therebetween. Optionally, the period is from 10 to 30 seconds. Optionally a period is 20 seconds.

A diaphragm 102 (and optionally 106) is coupled to an aerosol chamber 104 and acoustically coupled to an acoustic energy generator 100. A diaphragm is made of any material suitable for transferring acoustic energy from the acoustic energy generator 100 to a substrate material for the generation of aerosol. Illustrative examples of materials suitable for use as a diaphragm include latex, nitrile, vinyl, other polymeric materials, or other material known in the art. A diaphragm has a thickness. A diaphragm thickness is optionally from 0.001 to 0.1 inches or any subdivision therebetween. The thickness, elasticity, and rigidity of a diaphragm are limited only by the ability of the diaphragm to translate acoustic energy from the first side of the diaphragm to the second side of the diaphragm at sufficient amplitude to generate an aerosol in an aerosol chamber. It is appreciated that when a diaphragm is coupled to an aerosol chamber any stretching of the material does not allow aerosol or substrate material to penetrate the diaphragm. This increases the safety of a user by preventing unwanted exposure to aerosols or substrate material. Thus, a diaphragm is comprised of material that prevents significant penetration by aerosol particles or substrate material. A diaphragm is optionally coupled to an aerosol chamber using an elastic material such as a rubber o-ring, band, clamp, adhesive, or other method recognized in the art.

An aerosol chamber 104 defines a space with internal atmospheric pressure that is optionally tunable relative to the space external to the aerosol chamber. To achieve the enclosed internal space an aerosol chamber 104 includes a first end and a second end disposed substantially along a longitudinal direction. A first end is enclosed by a first diaphragm 102. A second end is optionally enclosed by the shape of an aerosol chamber or by a second diaphragm 106. A second diaphragm is optionally of the same material and dimensions as a first diaphragm, the same material as the aerosol chamber, a different material, or combinations thereof. In some embodiments, the second end is comprised of a second diaphragm 106 that is of the same material and thickness as the first diaphragm 102.

An aerosol chamber 104 is made from any material suitable to produce a rigid chamber. Illustrative examples include any thermoplastic or thermoset material, illustratively acrylics, epoxies, polyesters, or other polymeric materials, stainless steel, glass such as borosilicate glass, or other suitable material known in the art. An aerosol chamber is optionally transparent to allow visual monitoring of aerosol formation or substrate depletion.

An aerosol chamber 104 has any shape and dimension operable for the generation of particulate aerosols. Optionally, an aerosol generator is cylindrical, conical, irregular, rectangular such as box shape, or other shape. An aerosol chamber 104 optionally has a cross section whereby the cross section is optionally: circular; oval; square; rectangular; trapezoidal; polygonal such as pentagonal, hexagonal, octagonal, or other polygon; or other cross sectional shape. In some embodiments the cross sectional area differs at different longitudinal distances from a first diaphragm.

Illustrative dimensions of an aerosol chamber are from 1 to 30 inches in height and 0.5 to 25 inches in diameter or cross sectional length. Any height or length therebetween or range therebetween are similarly operable. The dimensions of the chamber are appreciated to be any length, height, or cross sectional area operable to house a sufficient amount of substrate material to generate aerosols for a desired amount of time at a desired concentration.

The atmospheric pressure within the aerosol chamber or outside the aerosol chamber is optionally tunable. In some embodiments, the atmospheric pressure on the second side of the first diaphragm 102 (i.e. within the chamber) is higher than the atmospheric pressure on the first side of the first diaphragm 102. When the atmospheric pressure is greater on the second side of the first diaphragm 102 the pressure differential forces the diaphragm into a slightly concave shape allowing the substrate material to focus into a focal zone that may increase the efficiency of the generator. It is appreciated that the diameter of the focal zone is optionally less than 10 percent the diameter of the first membrane, optionally 15%, 20%, 25%, 30%, 35%, 40%, 50% 70%, 90%, or a any subdivision therebetween, the diameter of the first diaphragm. In some embodiments the focal zone has a diameter in excess of 2 centimeters. The diameter of the focal zone is adjustable by the differential atmospheric pressure of within the aerosol chamber relative to the external atmospheric pressure.

In some embodiments the atmospheric pressure on the second side of the first diaphragm differs from the atmospheric pressure on the first side by −0.3 to 0.5 inch-$H_2O$. Optionally, the atmospheric pressure on the second side of the first diaphragm is 0.1 inch-$H_2O$ greater than the atmospheric pressure on the first side.

The atmospheric pressure on either side of the first diaphragm 102 is illustratively regulated by placing the aerosol chamber in an enclosure 124. Both the atmospheric pressure in the aerosol chamber 104 and the enclosure 124 are optionally tunable independently and relative to one another by use of one or more mass flow controllers, relief ports, or other valving, pumping, or release systems. The atmospheric pressure is optionally regulated by one or more pumps to provide air or other gas pressure to an atmospheric pressure regulation system. In some embodiments a pressure regulator 108 is provided that pumps house air or other gas or combination of gasses toward an aerosol chamber 104 through one or more conduits.

One or more mass flow controllers 116, 118, regulate the amount of gas transferred to the interior of the aerosol chamber 104 and the interior of the surrounding enclosure 124. A mass flow controller is illustratively obtained from Aalborg (model # GPC373S). A first mass flow controller 116 optionally delivers gas to an aerosol chamber at a constant flow rate or a variable flow rate. A second mass flow controller 118 optionally delivers gas to an enclosure at a constant or a variable flow rate. In some embodiments, a first mass flow controller 116 delivers gas to an aerosol chamber 104 at a rate of 2-10 LPM, optionally 6 LPM. A second mass flow controller 118 delivers gas to an enclosure 124 at a variable rate optionally 0-30 LPM. It is appreciated that the atmospheric pressure on the first side of the first diaphragm 102 and the second side of the first diaphragm 102 is tunable by varying the gas flow rate from either the first mass flow controller 116, the second mass flow controller 118, or both. Optionally, an enclosure is fitted with a relief port 130 that regulates the pressure of gas within an enclosure 124 thereby regulating the pressure therein.

The gas pressure moves into the system via an optional pressure regulator 108 on a conduit. A conduit optionally includes one or more dryers 110 to remove or otherwise regulate the moisture content of the gas flowing into the remainder of the system. It is appreciated that gas may be delivered to a conduit from a pre-pressurized source such as a tank whereby the rate of gas flow is controlled by a regulator in line with the tank.

One or more filters are also provided in line with the conduit to remove particulate or other contaminants from the gas flowing into the aerosol generator. Illustrative filters include a charcoal filter 112, and a HEPA filter 114. While FIG. 1 illustrates the relationship of a dryer 110, charcoal filter 112, and HEPA filter 114 in a linear order, this order is for illustrative purposes only. Other orders, or a plurality of one or more filters or filter types or dryers are similarly within the scope of the invention. Sources of filters and dryers such as dehumidifiers are known in the art.

The embodiment illustrated in FIG. 1 illustrates a conduit splitting into two sections for delivery of gas to a first mass flow controller (MFC) and a second MFC. It is appreciated that each MFC is optionally supplied by independent gas sources. Optionally, each MFC is supplied by a different gas type. Optionally, a first MFC delivers purified nitrogen, oxygen, or other purified gas or plurality of gasses, or house air to the interior of an aerosol chamber 104. A second MFC optionally delivers purified nitrogen, oxygen, or other purified gas or plurality of gasses, or house air to the interior of an enclosure 124. Should the aerosols generated be more suspendable, or generatable in a purified gas, cost savings are appreciated by delivering the purified gas to the aerosol chamber 104 and house air to the surrounding enclosure 124.

An aerosol chamber 104 or an enclosure 124 optionally includes one or more pressure sensors 128. A pressure sensor provides real time feedback to a user, or a computer system 148, or both of the pressure within the aerosol chamber 104 or the enclosure 124. This allows adjustment of the pressure in multiple locations for differential aerosol generating conditions.

The aerosol generator is capable of ramping up aerosol generation from zero to a target aerosol concentration in less than 15 minutes, optionally less than 10 minutes, optionally, less than 5 minutes, optionally less than 2 minutes, or any range or value therebetween.

The aerosols produced by an aerosol generator are optionally transferred via a conduit to an exposure chamber 134. An exposure chamber 134 is suitable for housing one or more subjects during experimental aerosol exposure time. An exposure chamber 134 optionally includes a temperature sensor 138, an exposure chamber pressure sensor 142, and a nephelometer 136 to measure the concentration of aerosol present in the exposure chamber. An example of a nephelometer is a DataRAM available from Thermo Fisher Scientific Inc., Waltham, Mass. An exposure chamber 134 optionally includes one or more humidification controllers 140. A humidification controller is optionally a humidifier illustratively a damp sponge or other humidifier known in the art, dehumidifier, or other humidification control system known in the art.

An exposure chamber 134 is atmospherically coupled to an aerosol chamber 104. Atmospheric gas containing aerosol moves from an aerosol chamber 102 illustratively through one or more conduits to an exposure chamber 134. The flow of aerosol to an exposure chamber is optionally regulated by several systems illustratively including the rate of aerosol generation tunable by adjustments of the acoustic energy generated by an acoustic energy generator 100, the flow rate of gas into an aerosol chamber 104, the diameter or other cross sectional area of a conduit connecting an exposure chamber 134 and an aerosol chamber 104, a gas flow restriction system, additional gas delivered downstream of the aerosol generator, or other system known in the art.

An exposure chamber optionally includes one or more sensors to determine the atmospheric conditions or level of aerosol in an exposure chamber. Optionally, an exposure chamber includes one or more temperature sensors 138, pressure sensors 142, nephelometers 136, humidifiers or dehumidifiers, or other sensor or atmospheric regulator known in the art.

In some embodiments a plurality of exposure chambers are atmospherically connected to an aerosol chamber. Optionally, 2, 3, 4, 5, 6, or more exposure chambers are simultaneously or sequentially connected to an aerosol chamber so as to allow a larger number of subjects to be studied.

Delivery of aerosols to an exposure chamber is optionally continuous or intermittent. An atmospheric flow restrictor is optionally present that restricts the flow of aerosol from an aerosol chamber to an exposure chamber.

An exposure chamber allows aerosols to flow through the chamber and exit. An exit conduit optionally includes a filter, illustratively a HEPA filter that removes aerosols from the gas prior to venting the gas into a room or its collection. A third MFC 120 optionally regulates the flow of gas from the exposure chamber. An exit conduit is optionally connected to a vacuum source to assist drawing aerosols from an aerosol chamber 104, an exposure chamber 134, or any conduit.

The aerosol generator of the invention is capable of tightly regulating the level and characteristics of aerosols generated and delivered to an exposure chamber. The tunability of the acoustic energy generator 100 combined with the gas flow rate into an aerosol chamber and controllable differential atmospheric pressure on the second side of a first diaphragm and the first side of a first diaphragm allows continuous adjustment of the level and physical characteristics of aerosols produced by the system. An aerosol generator is capable of producing particulate aerosols at a concentration from 0.1 to 12 mg/m$^3$. The range of 0.1 to 12 mg/m$^3$ is adjustable to any level or range of levels therebetween. Optionally, greater than 12 mg/m$^3$ of aerosol is generated by the aerosol generator, illustratively as much as 20 mg/m$^3$ or more. In some embodiments the concentration of aerosols are from 5 to 12 mg/m$^3$, or any subdivision therebetween. It is appreciated that higher concentrations of aerosols are possible.

It is appreciated that an aerosol generator is capable of producing aerosols at a constant concentration for 30 or more hours. Typical times for constant aerosol concentrations are from 2 to 10 hours. Optionally, aerosol concentrations are maintained at a constant level for 5 hours. As used herein "constant" levels of aerosols is meant to describe variation from a target or average aerosol concentration of 20 percent or less, optionally 10 percent or less, optionally 5 percent or less, optionally 3 percent or less, optionally 2 percent or less, or any range or value therebetween. In some embodiments aerosols are maintained to a concentration varying less than 2 mg/m$^3$ when run at a target concentration of 10 mg/m$^3$ for at least 1 hour.

It is appreciated that a measured concentration deviates 2 percent or less of target aerosol concentrations with the generator even at high aerosol concentrations of 6, 10, or 12 mg/m$^3$. A substrate material is any material suitable for generating aerosols.

Aerosols are optionally particulate aerosols. Any substrate operable to produce a particulate aerosol may be used. An illustrative substrate material is multi-walled carbon nanotubes (MWCNT) bulk material. MWCNT is illustratively available from Mitsui & Co, Ibaraki, Japan. Other illustrative substrates include silica powder, bulk cotton dust, titanium dioxide powder, mold spores, wood dust, moldy hay particulate, polystyrene particles, or other dry powder or dust particulate substrate material.

The generation of aerosols is optionally regulated by a computer controlled system and is, therefore, automatic or partially automatic. A generator is optionally electrically coupled to a multi-purpose computer specially programmed to control optionally: gas pressure entering the aerosol chamber 104 such as via regulating a first MFC 116; gas pressure entering the enclosure 124 such as via regulating a second MFC 118; detecting the pressure in the aerosol chamber 104; detecting the pressure inside the enclosure 124; adjusting the characteristics of the acoustic energy generated (i.e. period, amplitude, frequency range, etc.); determining the temperature in an exposure chamber 134; detecting the humidity in an exposure chamber 134; detecting the gas pressure in an exposure chamber 134; or detecting the level of aerosol in the exposure chamber 134, the aerosol chamber 104, regulating the rate of gas release from an exit conduit via a third MFC 120, or combinations thereof.

A proportional-integral-derivative (PID) control algorithm similar to that described by Nise, Norman S., Control Systems Engineering—2$^{nd}$ ed. Addison-Wesley Publishing Company, Menlo Park, Calif., 1995, the contents of which are incorporated herein by reference, is optionally used to control each MFC, the acoustic energy generator, pressure regulators, and detectors in an aerosol generator and exposure chamber system. The constants $P_{gain}$, $I_{gain}$ and $D_{gain}$ used by each PID control loop are found using basic control tuning methods described by Nise. The interface with the computer system is illustratively designed with LabVIEW 7.1. Methods of designing control algorithms are well known in the art.

A process for exposing a subject to an aerosol is also provided. A subject as used herein is any biological organism. Illustrative examples of a subject include animals such as a human or non-human primate, murine such as a rat or mouse, equine, sheep, pig, bovine, hamster, guinea pig, rabbit, a cell, a tissue, or other organism that may or may not generate a biological response to aerosol exposure.

A process for exposing a subject to an aerosol optionally includes placing a subject in an exposure chamber that is atmospherically coupled to an aerosol generator (i.e. to an aerosol chamber) and exposing the subject to an aerosol, optionally multi-walled carbon nanotubes, produced by the generator. The ability of the aerosol generator as described herein to tightly control the exposure level and characteristics of the aerosols generated allows an inventive process to include exposing the subject to aerosols at a concentration of between 0.001 to 12 mg/m$^3$ for an exposure period. An exposure period is optionally at least one hour. Optionally, an exposure period is any time less than 30 hours. It is appreciated that an exposure period is limited only by the supply of substrate material in an aerosol generator and as such can be shorter or longer than that described. As the substrate material is optionally replenishable during an aerosol generating process, the exposure period is essentially unlimited.

A subject is optionally exposed to a constant concentration of aerosol. A constant concentration is optionally as described herein. Optionally, a subject is exposed to a concentration of aerosol that is maintained to within 20 percent of average or target exposure concentration during the exposure time. The level of aerosol is optionally detected by a nephelometer that is electrically connected to a programmed computer. The programmed computer optionally adjusts the level of aerosol exposure to a subject by adjusting the pressure differential across a first diaphragm, the frequency or period of acoustic energy, or other parameter.

The aerosols produced in an aerosol chamber are optionally separated by elutriation. A conduit connecting an aerosol chamber and an exposure chamber is, therefore, optionally connected at a point sufficiently above the first diaphragm such that aerosols with desired characteristics such as small size are moved from the aerosol chamber to an exposure chamber. As used herein small with respect to aerosol size is defined as aerosol particles with an aerodynamic diameter of 5 micrometers or less. Larger particles consisting of agglomerated fibers and bundles stay in the lower portion of the aerosol chamber until being dispersed. While the exact location of the conduit connecting the aerosol chamber and the exposure chamber is variable, the gas flow rate into the aerosol chamber as controlled by the first MFC can be used to tune the elutriation of the particles. Increasing the gas flow rate will push larger particles or agglomerated fibers into the upper chamber region causing them to transfer to an exposure chamber. For an exposure chamber with a vertical dimension of 18 inches and a diameter of 14 inches, keeping the gas flow rate at or below 15 LPM will separate the larger particles from the aerosols.

An inventive process optionally includes varying the frequency above and below the resonant frequency of the acoustic energy translating surface. The acoustic energy is optionally focused or unfocused. The frequency of the acoustic energy optionally oscillates in a frequency range of less than 1000 Hz, optionally less than 20 Hz.

Various aspects of the present invention are illustrated by the following non-limiting examples. The examples are for illustrative purposes and are not a limitation on any practice of the present invention. It will be understood that variations and modifications can be made without departing from the spirit and scope of the invention.

EXAMPLES

Example 1

Figure 2:
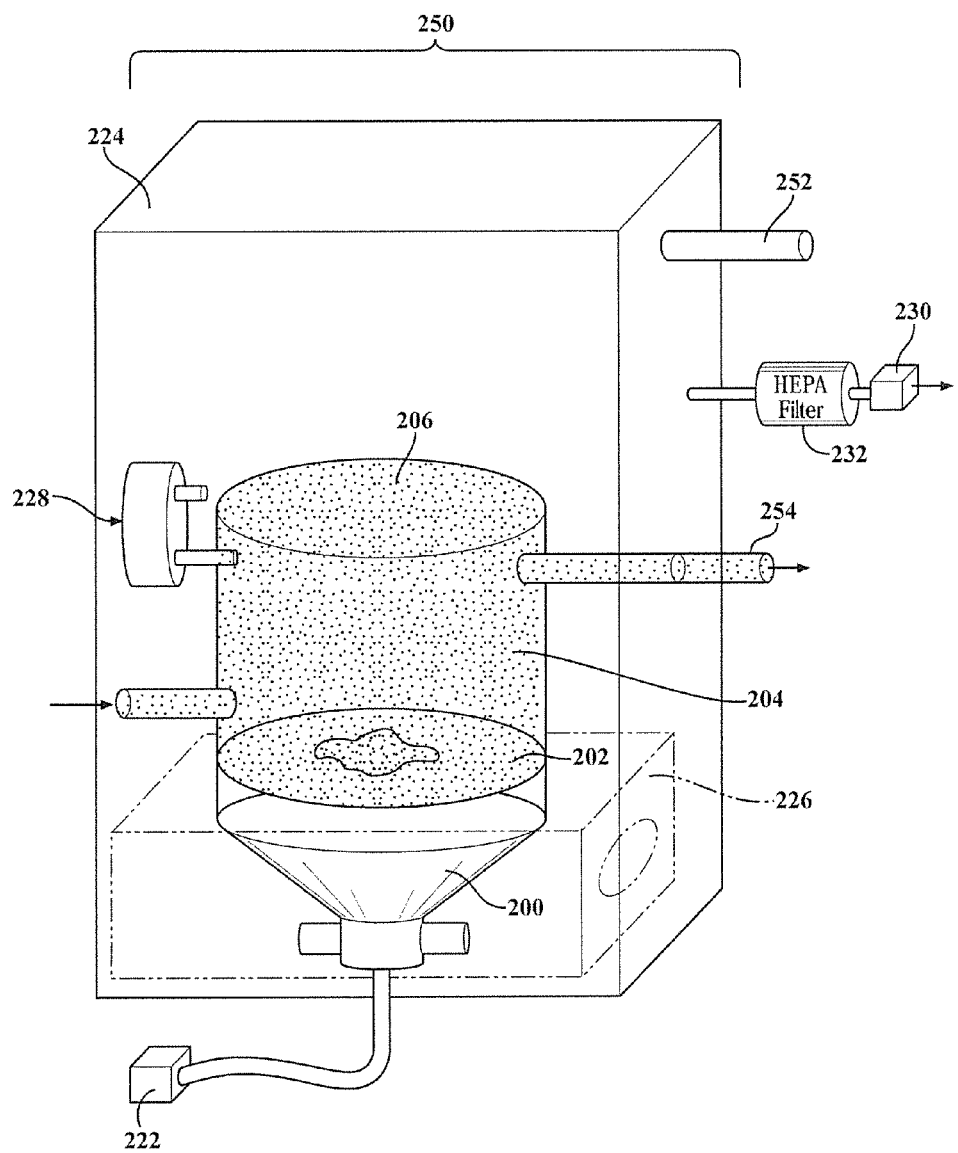
FIG. 2 is a schematic of an aerosol generator according to one embodiment of the invention.

Construction of an aerosol generator. An exemplary aerosol generator 250 is depicted in FIG. 2. A major component of the generator is a large cylindrical acrylic chamber 204. An aerosol chamber 204 is constructed of cylindrical acrylic with a height of 18 inches and a diameter of 14 inches. The walls of the acrylic cylinder, excluding a viewing port, are lined with conductive foil tape and are electrically grounded to prevent the build up of static electrical charge. Both ends of the cylinder are enclosed with flexible latex rubber diaphragms 202, 206 to form a drum-like structure. A first diaphragm 202 is located on a lower end of the cylinder and a second diaphragm 206 is located on the upper end of the cylinder. Each diaphragm is made of latex with a mean stretched thickness of 0.02 inches. Each diaphragm is affixed to the cylinder by a rubber o-ring.

The aerosol chamber 204 with two diaphragms 202, 206 is mounted vertically above a speaker enclosure 226 containing a high compliance 15 inch loudspeaker (Ciare, model #15.00SW) to act as an acoustic energy generator 200. The loudspeaker 200 is placed in an upward facing position physically remote from bottom diaphragm 202 of the aerosol chamber 204. An amplifier is electrically connected to the loudspeaker 200 to control the variable frequency of acoustic energy emitted by the loudspeaker.

Clean, filtered, dry house air is supplied to the interior volume of the aerosol chamber 204. A conduit 254 is placed substantially opposite the first diaphragm 202 on the upper outer surface of the chamber 204 to carry aerosols away from the interior volume of the aerosol chamber.

The loudspeaker 200, speaker enclosure 226, and chamber 204 are placed in a surrounding enclosure 224 (48×20×20 inches) so that gas pressure can be tuned and maintained at a relative level across the diaphragms and the exterior of the cylinder. The enclosure provides: 1) muffling the acoustic noise produced by the loudspeaker; 2) a barrier to protect operators from aerosols that escape from the generator due to a leak or ruptured diaphragm; and 3) precise control of the pressure differential across the flexible diaphragms on the ends of the cylinder. A pressure sensor 228 is located on the wall of the cylinder to monitor the trans-diaphragm pressure. An enclosure relief port 230 coupled to a filter 232 is located on the outer enclosure 224. This relief port is optionally regulated to release gas pressure from the interior of the enclosure.

Example 2

Generation of aerosols within an aerosol generator. Bulk samples of multi-walled carbon nanotubes (5 grams) are placed inside the aerosol chamber of the aerosol generator of Example 1 and onto the lower diaphragm. The speaker is driven with a computer generated analog signal fed through an audio amplifier (Butt Kicker, Model #BKA-1000-4A). The signal used to excite the speaker consists of a variable frequency sine wave that gradually sweeps back and forth between 10 and 18 Hz over a 20 second period to generate frequencies above and below the resonant frequency of the acrylic cylinder and flexible diaphragm combination. A sweeping voltage signal has the advantage of compensating for changes in the chamber and diaphragm resonance frequency while still moving through the new resonance frequency thereby improving overall aerosol generation over time. Thus, slight changes in the actual resonance frequency (for example +/−3 Hz) of the generator has minimal effects on the overall output efficiency.

Figure 3:
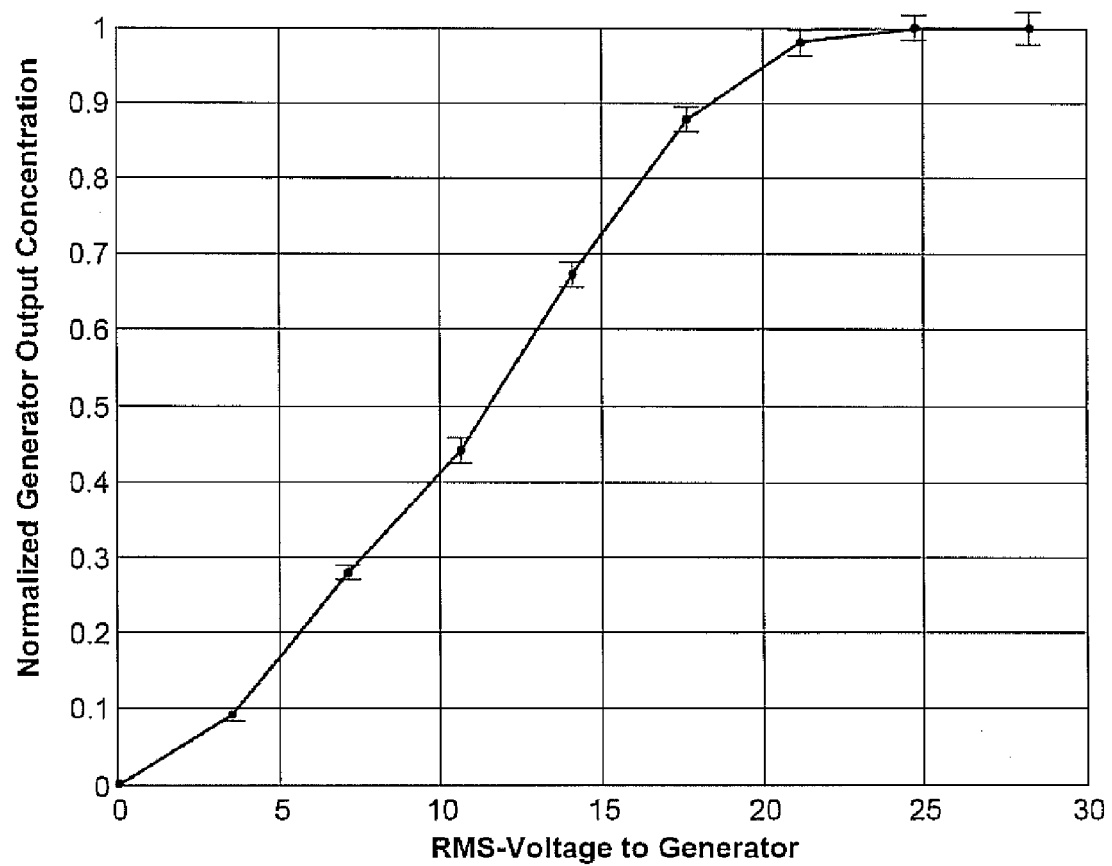
FIG. 3 represents the RMS voltage of acoustic energy generator excitation and the resulting aerosol output concentration.

The output concentration of the generator is controlled by varying the amplitude of the signal used to drive the speaker. The relationship between the RMS voltage of the speaker excitation and the generator aerosol output concentration is shown in FIG. 3. Each data point represents the mean concentration at the set RMS voltage over a 30 minute run period. The error bars indicate the standard deviation of the concentration over the test period.

Figure 4:
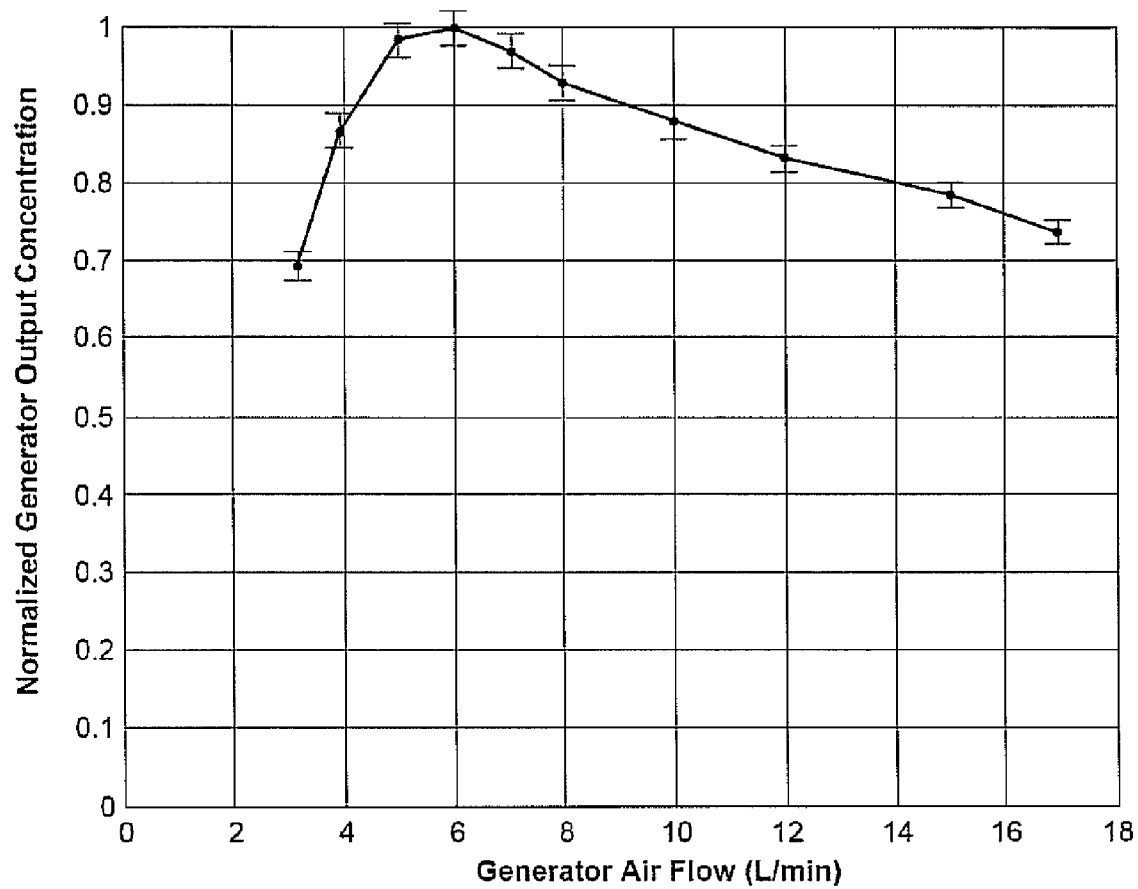
FIG. 4 depicts the relationship between generator air flow and aerosol output concentration.

Dried, filtered air enters the aerosol generator of Example 1 on the lower left hand side of the aerosol chamber, and exits the chamber on the upper right hand side. The vertical positioning of the chamber allows the produced aerosols to be separated by vertical elutriation allowing only small airborne particles to escape the cylinder. The relationship between generator air flows and generator output concentration is shown in FIG. 4. Each data point represents the mean concentration at the set generator air flow rate over a 30 minute run period. The error bars indicate the standard deviation of the concentration over the test period. The aerosol output drops off quickly and low airflow rates. At high airflow rates, the concentration of aerosols is diluted by the excess air. In order to maximize the generator's performance, it is typically operated at 6 LPM.

The larger particles consisting of agglomerated fibers and bundles stay in the lower portion of the cylinder until being dispersed. When the generator air flow rate is increased to levels above 15 LPM, larger particles could exit the generator and distort the desired aerosol size distribution. In order to keep the larger agglomerated bundles from escaping the generator, the generator airflow does not exceed 15 LPM with the exemplary dimensions of the aerosol generator.

Figure 5:
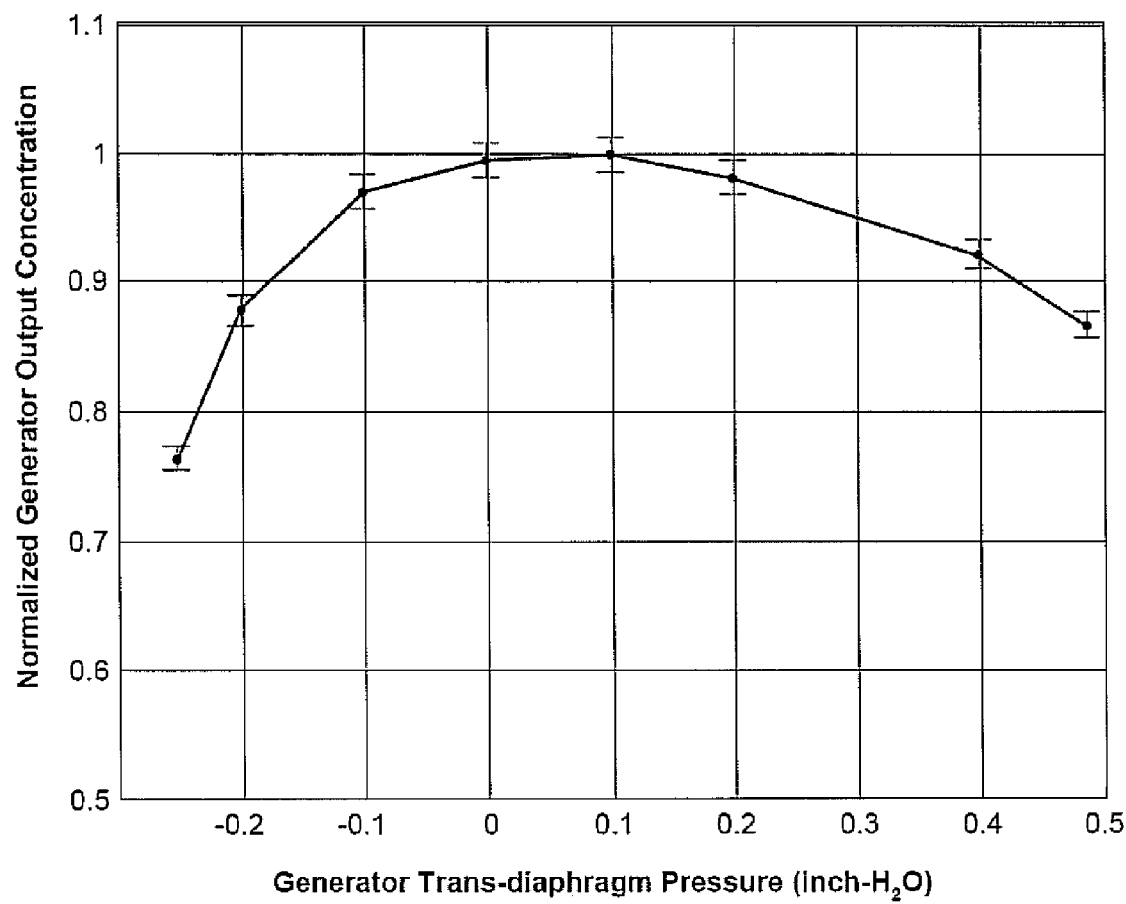
FIG. 5 depicts aerosol output concentration as a function of trans-diaphragm pressure.

The pressure inside the generator's cylindrical chamber increases quickly as air flows through it, through several feet of tubing, through the exposure chamber, and finally through a HEPA filter before it is exhausted. Controlling this pressure regulates the two flexible membranes on the ends to allow them to bulge outward, inward, or remain flat. An outward bulging (concave inner surface) causes the substrate material to collect at the center of the lower diaphragm into a small focal zone. Since most of the displacement acoustic energy is delivered to that portion of the diaphragm, a slightly positive pressure across the flexible diaphragm provides improved generator performance. At excessive positive pressures the flexible diaphragms become overly stretched and less compliant resulting in a reduction in generator efficiency. By regulating the pressure inside the aerosol chamber, the adverse effects of the pressure differential acting on the flexible diaphragms is controlled to maximize the generator's performance. The pressure difference across the diaphragms is measured with a pressure transducer (Setra, model #264). The generator normalized aerosol output concentration as a function of trans-diaphragm pressure is depicted in FIG. 5. Each data point represents the mean concentration at the set trans-diaphragm pressure over a 30 minute run period. The error bars indicate the standard deviation of the concentration over the test period. At negative pressure differences the flexible diaphragms are pulled toward the inner portion of the aerosol chamber causing the bulk material on the lower diaphragm to migrate toward the edges resulting in a decrease of the aerosol output concentration. The MWCNT system uses a computer controlled automated feedback loop to maintain the trans-diaphragm pressure at its optimal value of +0.1 inch-$H_2O$. This ensures the generator operates near its maximum effectiveness and eliminates pressure related fluctuations in the output concentration.

Example 3

Automatic control of aerosol generation. A computer is specially programmed to regulate aerosol generation and subsequent aerosol concentrations in an exposure chamber. Three different feedback loops are used to control: the subject exposure concentration; the exposure chamber pressure; and the generator's trans-diaphragm pressure. The exposure concentration is maintained at a constant value by making adjustments every 20 seconds to the amplitude of the particle generator's excitation voltage based on readings made from the DataRAM nephelometer. Typical exposure concentrations range between 5 and 12 mg/m$^3$.

The exposure chamber pressure is regulated by making corrections to the exposure chamber exhaust flow once every 2 seconds based on readings from a Setra pressure transducer. The exposure chamber pressure is typically held constant at a slight negative value of −0.02 inches of $H_2O$.

The trans-diaphragm pressure differential is automatically controlled by making adjustments to the amount of air entering the generator enclosure box, which also has a small relief port. A correction is made every 2 seconds based on the output of the Setra pressure transducer within the enclosure box. The pressure differential across the generator diaphragms is typically held constant at +0.1 inches of $H_2O$ to yield maximum generator output efficiency.

Figure 6:
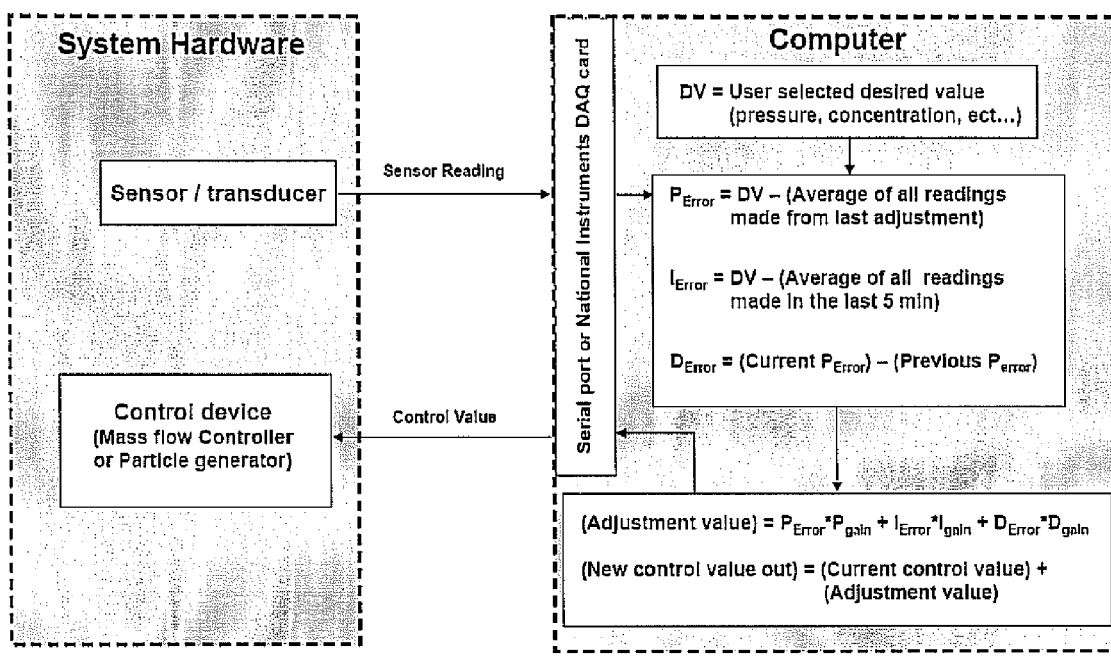
FIG. 6 is a schematic of a feedback control algorithm of a computer controlled aerosol exposure system.

A proportional-integral-derivative (PID) control algorithm, Nise, 1995, is implemented for each feedback control loop employed by the MWCNT exposure system. A block diagram of the feedback control algorithm is shown in FIG. 6. The constants $P_{gain}$, $I_{gain}$ and $D_{gain}$ used by each PID control loop are determined using basic control tuning methods described by Nise (1995).

Figure 7:
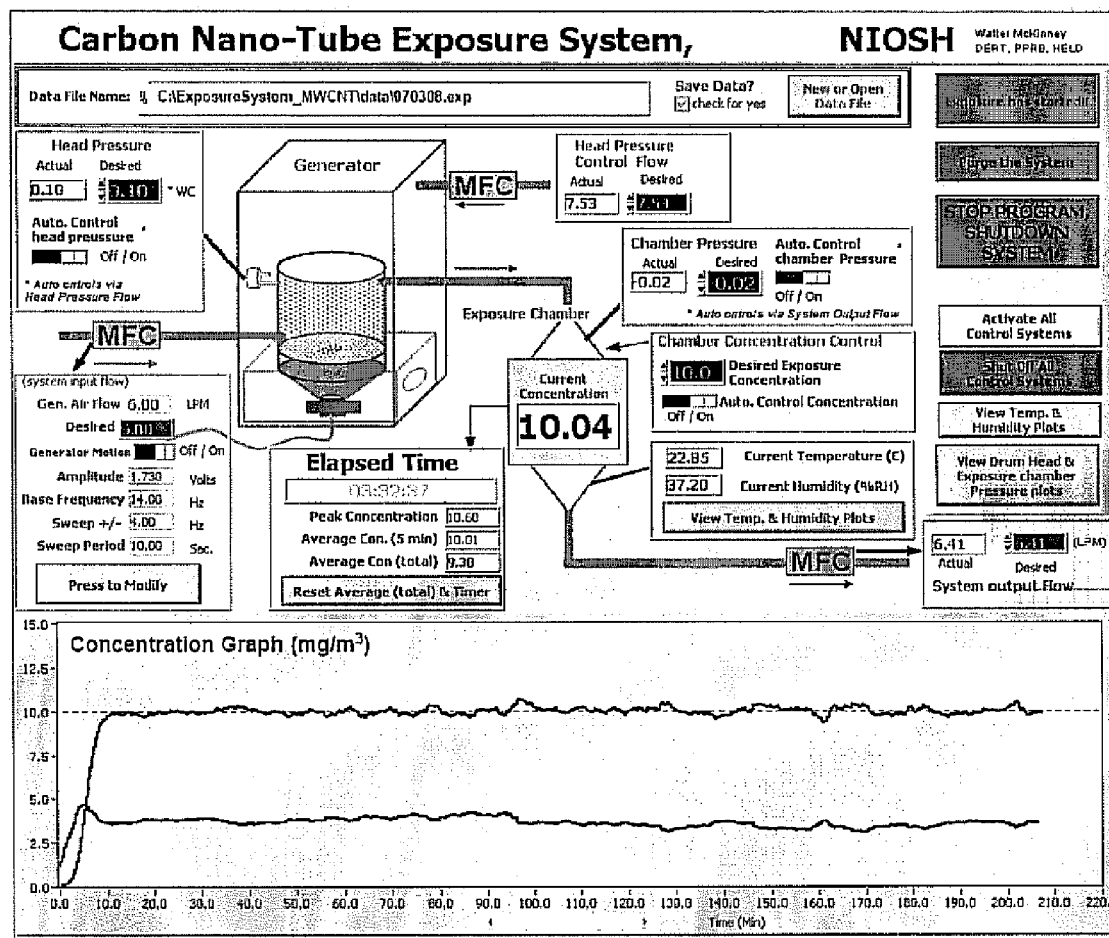
FIG. 7 is a schematic of a virtual instrument for monitoring and manual adjustment of one or more parameters regulating aerosol generation or exposure chamber concentrations.

A computer user interface is produced using the LabVIEW 7.1 programming environment to produce a virtual instrument as depicted in FIG. 7. A graphical display on the lower portion of the virtual instrument continuously displays the exposure concentration, the desired exposure concentration, and the output voltage driving the power amplifier of the acoustic energy generator. Three mouse-activated virtual buttons in the upper right hand corner of the user interface provide the main controls for the exposure system. After animals are placed into the exposure chamber, the top button, labeled "Start the exposure," is pressed, which immediately changes that button's label to "Exposure has started!!" The virtual instrument then prompts the user to select a data file name and the desired exposure concentration. After entering those parameters, all feedback control systems are enabled and average aerosol concentration over the entire exposure period, the peak concentration, the last five-minute average concentration, and the total elapsed time displays are reset to zero. The time and exposure averages are continuously displayed by the virtual instrument while the system is running.

The computer saves the history of the exposure parameters in the selected data file at two second intervals. Exposure parameters include: the elapsed exposure time (seconds), the generator excitation (volts), the airflow through the generator (LPM), the generator trans-diaphragm pressure (inches-$H_2O$), the exposure chamber aerosol mass concentration (mg/$m^3$), the exposure chamber temperature (° C.), the exposure chamber relative humidity (%), and the exposure chamber pressure (inches-$H_2O$). During the inhalation exposure period of a subject, the computer automatically controls the airflow through the generator and exposure chamber, the exposure chamber pressure, the generator trans-diaphragm pressure, and the voltage driving the generator speaker to maintain a constant aerosol inhalation exposure. The system operator may periodically check the exposure system parameters to verify the system is operating properly and to collect filter samples via the sample port in the exposure chamber. When the desired exposure period is completed, the operator presses the second main virtual button labeled "Purge the system." This disables the particle generator drive and raises the air flow rate into the exposure chamber to 15 LPM, quickly reducing the exposure chamber aerosol concentration. When the concentration drops below 0.05 mg/$m^3$ a window appears on the computer monitor indicating that the exposure is complete and it is safe to remove the animals from the chamber. At the same time the data file that saves all the exposure data is closed, and the feedback control loops are deactivated. After the animals are removed from the exposure chamber, the operator presses the third main virtual button labeled "Stop Program, Shutdown system," which sets all the mass flow controllers to zero flow and closes the software program.

Example 4

Figure 8:
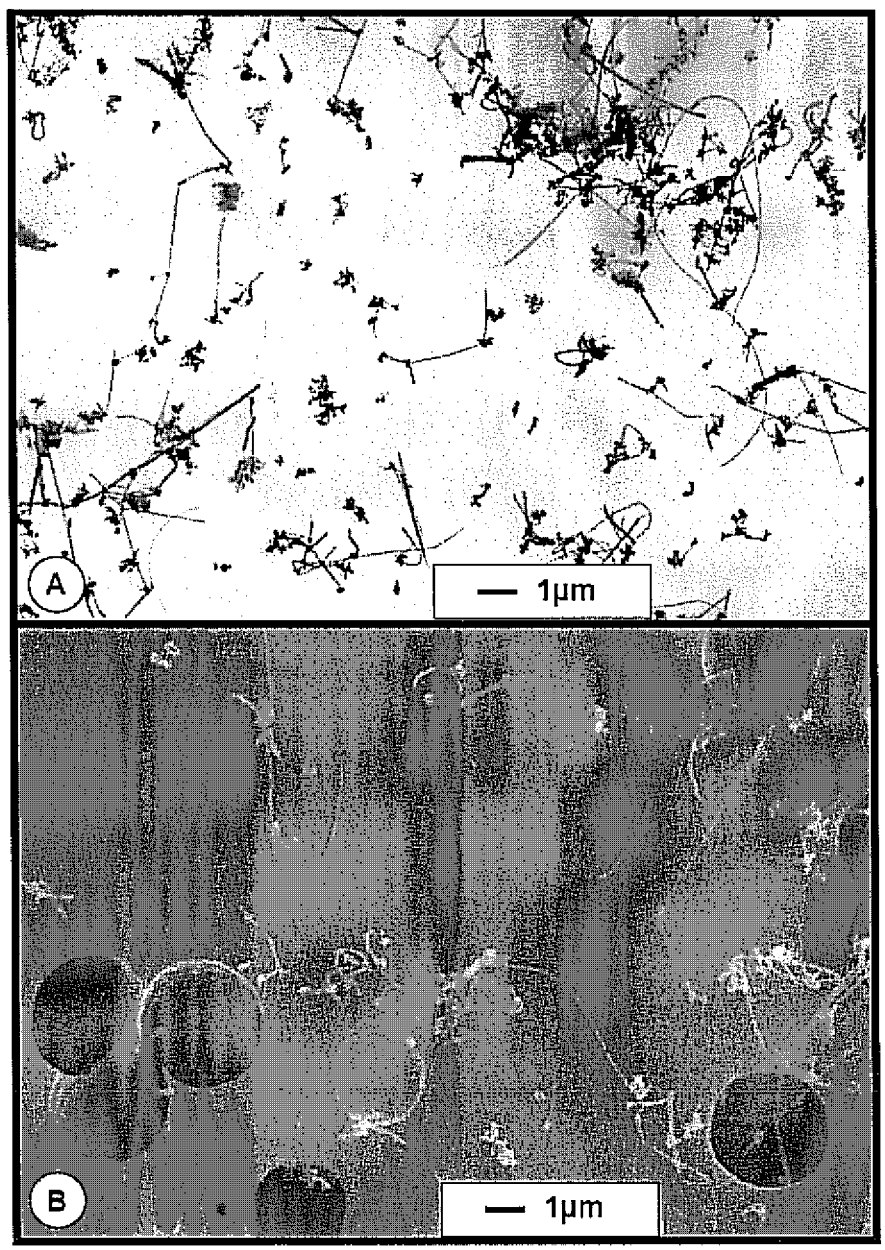
FIG. 8 illustrates representative aerosol particles from MWCNTs as detected by transmission electron microscopy (A) and scanning electron microscopy (B)

Aerosol physical characteristics. An exposure chamber capable of housing 6 mice is atmospherically coupled to the aerosol generator of Example 1 and the level of aerosols are regulated using the computer controlled system of Example 3. Aerosols are generated essentially as described in Example 2. The physical characteristics of the aerosols produced from MWCNT bulk material are measured and compared to MWCNT aerosols collected in an actual work environment. As a comparator, Han et al., *Inhalation Toxicology*, 2008; 20:741-749, incorporated herein by reference, collected samples from the breathing zones of a workplace producing MWCNT by drawing the aerosol through 35 mm filters at a rate of 1.5 L/min. The Han et al. workplace sample is compared with those obtained from the exposure chamber of the MWCNT inhalation system. The exposure chamber samples are collected by drawing aerosol from the chamber through 47-mm polycarbonate filters (Whatman, Clinton, Pa.) at a rate of 1 L/min. Those filters are then analyzed by transmission electron microscopy and scanning electron microscopy. (FIG. 8) The aerosols collected in the workplace by Han et al. (2008) and those illustrated in FIG. 8 show many small particles having nearly circular dimensions with diameters in the 100-300 nm range. These small particles appear to be composed of tangled knots of fibers. In addition to these particles, a distribution of dispersed and lightly agglomerated MWCNTs ranging in lengths from 1 to 6 µm, are present on both the workplace and exposure system samples. The particle size and shape appear nearly identical for samples collected in the workplace and in the exposure chamber.

Figure 9:
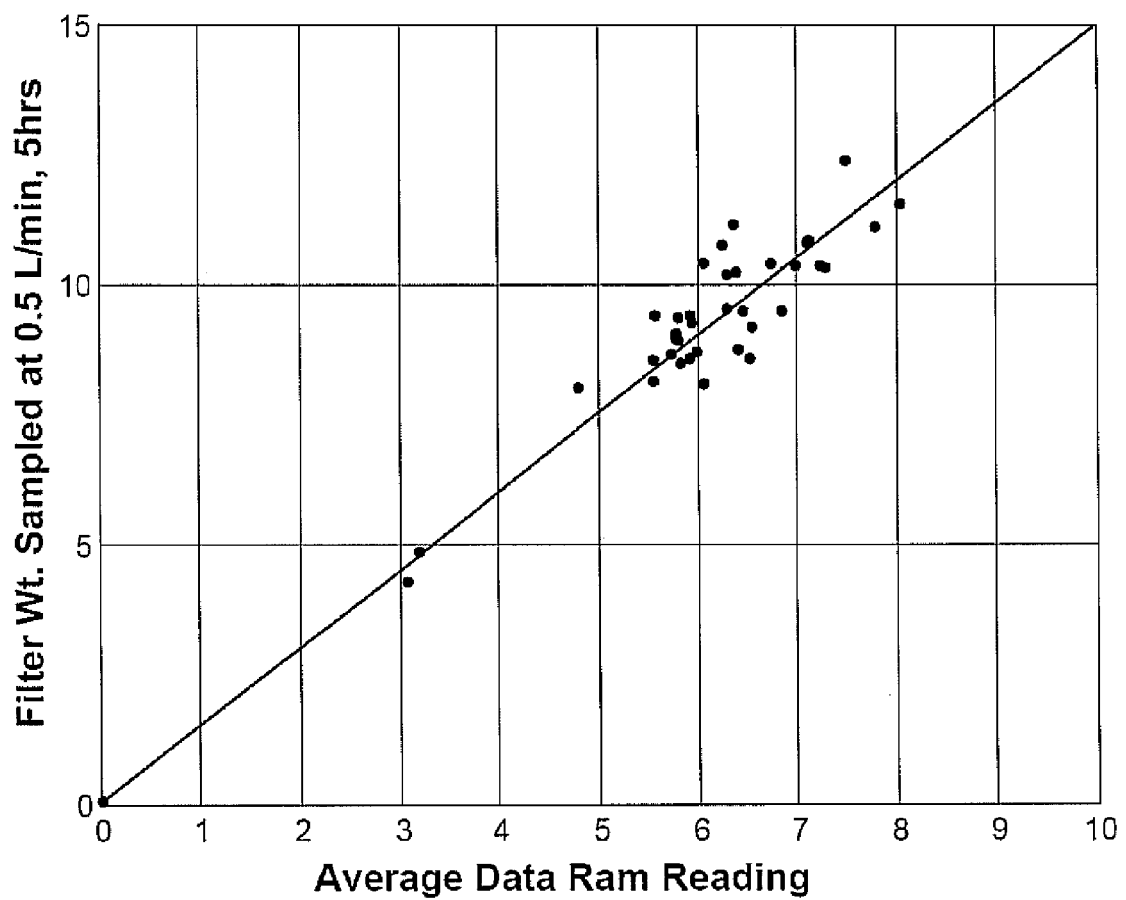
FIG. 9 illustrates the accuracy of aerosol concentration measurement by a nephelometer.

A DataRAM nephelometer is used to measure aerosol sizes within an exposure chamber or exiting an aerosol generator. To confirm that the nephelometer accurately measures particle concentrations, the output of a DataRAM is compared to the levels measured when collected on a filter. FIG. 9 illustrates the linear relationship indicating that the DataRAM is a suitable measurement device.

Example 5

Particle size distribution in an exposure chamber. The particle size distribution of the MWCNT in the exposure chamber ideally remains constant at all times to ensure that the same conditions can be reproduced during each exposure period. The only variable associated with exposures should be the user selected concentration (mg/$m^3$). Two types of experiments are performed to determine the particle size distribution of the output of the aerosol generator under different operating conditions. The first of these tests compares the size distribution of an aerosol generated with fresh bulk MWCNT powder (5 grams) with the size distribution of a MWCNT aerosol generated with the same powder after it had been used to produce a constant concentration of 10 mg/$m^3$ for 25 hrs. A second set of tests compares the particle size distribution of the generator output operating with a low energy signal (5.5 volts RMS, 25 W) verses a high energy signal (24 volts RMS, 100 W). This was important because the exposure concentration is controlled by varying the voltage delivered to the generator's speaker (FIG. 3).

Figure 10:
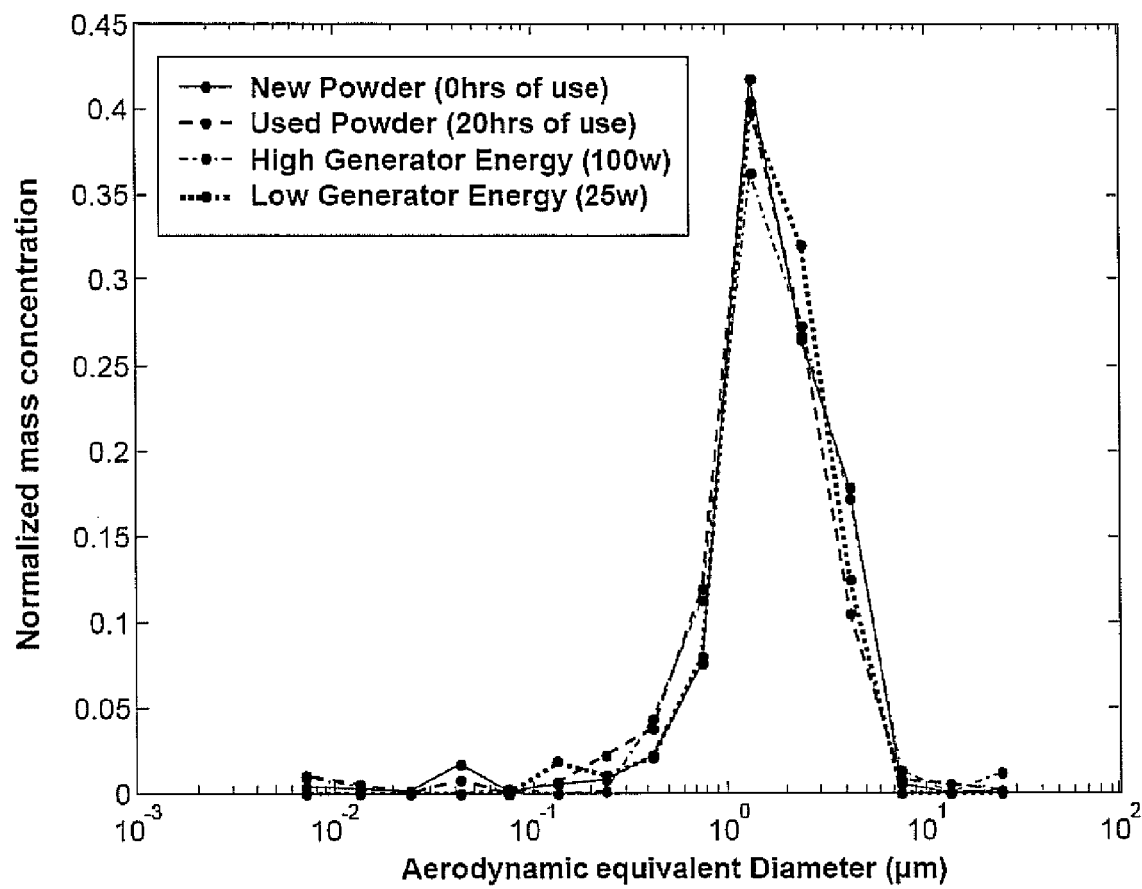
FIG. 10 illustrates aerosol particle size distributions as a function of substrate usage time and RMS voltage.

Particle size distributions are determined using a micro-orifice uniform deposit impactor (MOUDI Model 110) and a Nano-MOUDI (Model 115) to take exposure chamber samples during each test run. The results of the particle size distribution measurements are shown in FIG. 10. Surprisingly, no significant differences are observed between the four test samples. All samples have a mass median aerodynamic diameter of 1.5 µm. The particle distribution data could be characterized by lognormal curves, and the geometric standard deviations of all four curves are about 1.7. The particle count aerodynamic diameter mode is approximately 0.40 µm as determined by visually inspecting the MOUDI filters under a scanning electron microscope.

Example 6

Measurement of constant aerosol generation levels. A typical bulk sample of MWCNT material (5 grams) is used as substrate for generation of MWCNT aerosols in the aerosol generator of Example 1 by the process of Example 2. The generator produces a stable concentration of 10 mg/$m^3$ for a period up to 30 hrs. After 30 hrs the generator is operating at its maximum energy level (26v RMS, 113w) and producing concentrations slightly lower than 10 mg/$m^3$ illustrating that 5 grams of substrate material is sufficient to produce nearly constant levels of aerosols for as much as 30 hours without need for replenishment. Maintaining lower exposure chamber concentrations enables the 5 grams of MWCNT bulk material to produce a constant aerosol concentration over a longer period.

Example 7

Figure 11:
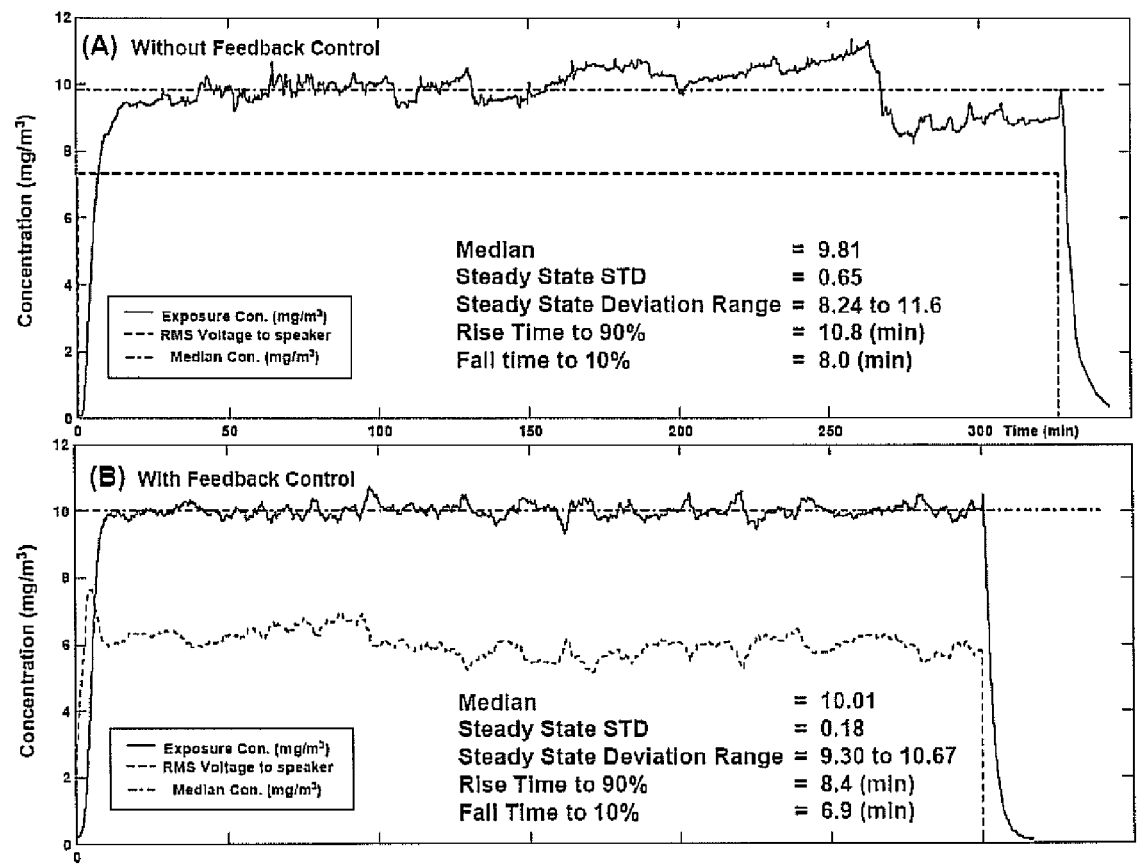
FIG. 11 depicts aerosol concentrations in an exposure chamber without (A) or with (B) automatic control.

Automatic control of aerosol levels in an exposure chamber. Bulk MWCNT substrate material is placed in the aerosol generator of Example 1 and aerosols are generated as in Example 2 with parameters controlled by the computer system of Example 3. The aerosol generator is operated for two 360 minute runs with and without the exposure concentration feedback control loops controlled by the computer system activated. The remaining two additional feedback control loops that control exposure chamber pressure and generator cylinder pressure are enabled during both runs. The target concentration in both cases is 10 mg/m$^3$. The automated control algorithm reduces the difference between the desired concentration and the median concentration by a factor of 19 (from 0.19 to 0.01), minimizes the fluctuation from the desired concentration by a factor of 3.6 (from 0.65 to 0.18), and reduces both rise time and fall times at the start and end of the exposure period by several minutes (FIG. 11).

Figure 12:
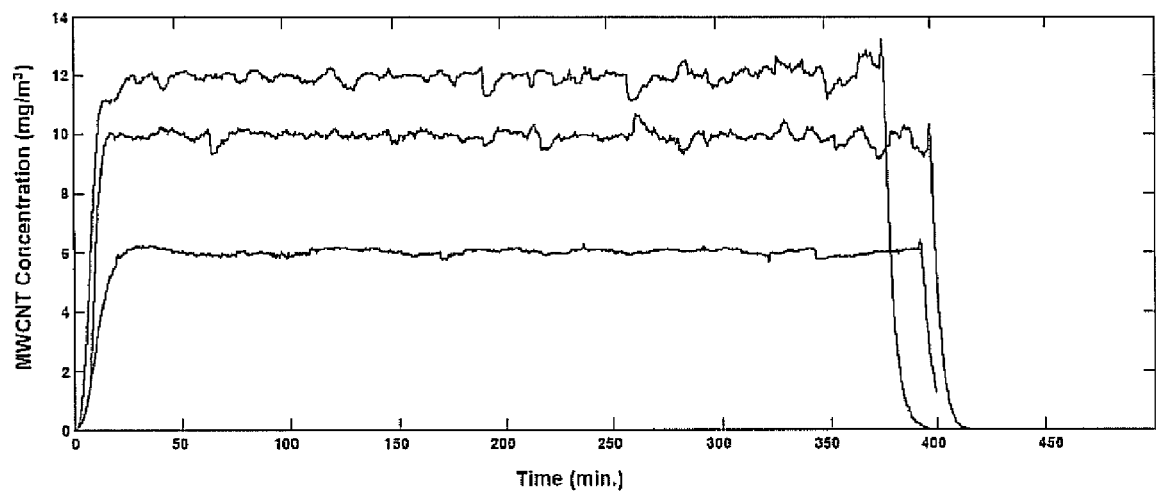
FIG. 12 depicts the constant levels of aerosol in an exposure chamber when generated at a target concentration of 6, 10, and 12 mg/m$^3$.

To verify that the computer controlled MWCNT system could automatically hold exposure levels at various user selected concentrations without an operator's assistance, three runs are performed with target aerosol concentrations of 6, 10, and 12 mg/m$^3$. The results of these test exposures are shown in FIG. 12 illustrating the constant level of aerosol over the entire test run.

Figure 13:
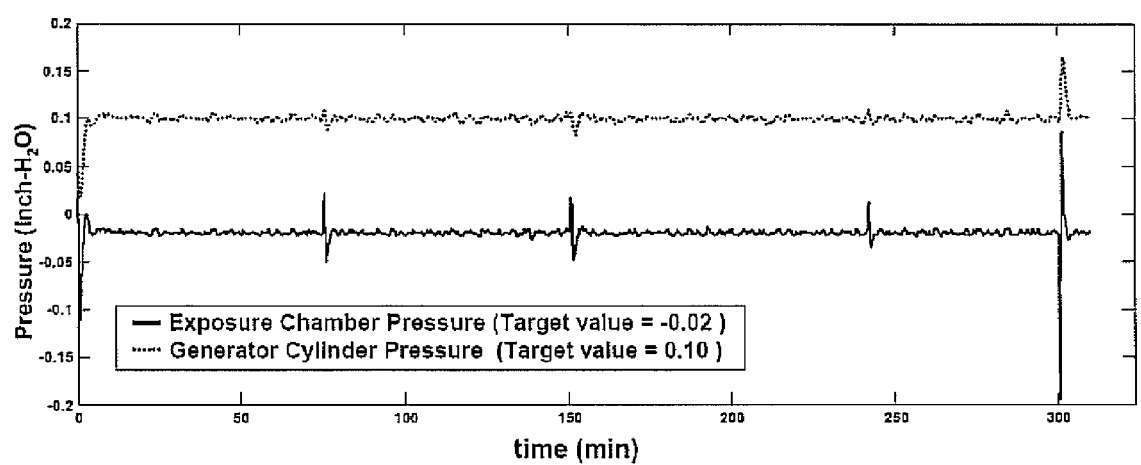
FIG. 13 illustrates the constant exposure chamber pressure and trans-diaphragm pressure over the course of an aerosol generating run.

The trans-diaphragm pressure is measured for the ability of the system to regulate a constant pressure across the diaphragms. The pressure inside the exposure chamber is held constant at −0.02 inch-H$_2$O relative to atmospheric pressure outside the exposure chamber and the aerosol chamber trans-diaphragm pressure difference is held constant at 0.10 inch-H$_2$O. The pressure measurements over a 300 minute exposure period are shown in FIG. 13. The automatically controlled aerosol generator is capable of automatically holding both pressures at very precise levels with a standard deviation of less than 0.003. The small blips on the exposure chamber pressure graph are a result of sample pumps being turned on and off during an exposure run as filters are being changed. The automatic control system quickly compensates for the variation in airflow leaving the exposure chamber during a filter change to bring the pressure back to the desired value.

Figure 14:
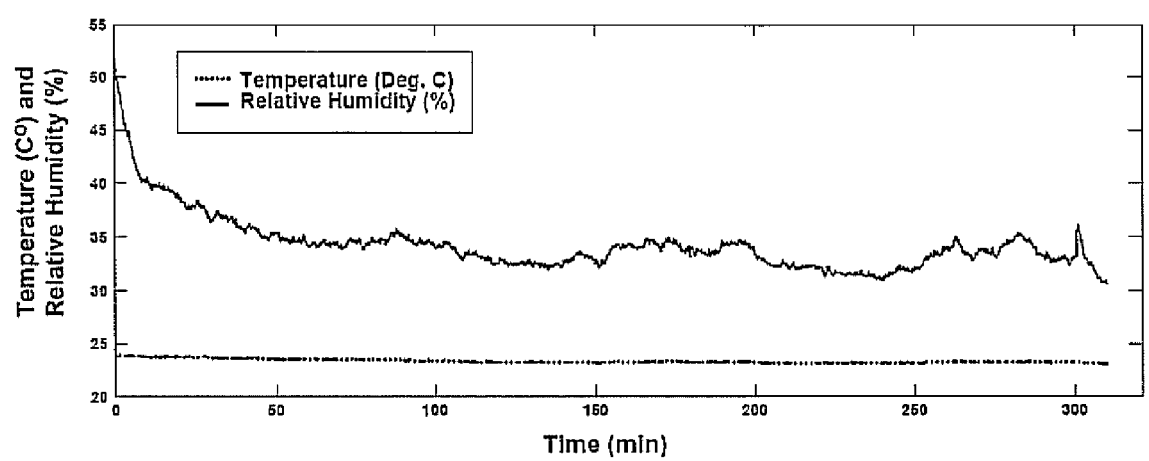
FIG. 14 illustrates the temperature and humidity data inside an exposure chamber for a typical exposure run lasting about 300 minutes.

The temperature and relative humidity inside the exposure chamber are not under feedback control in the exemplary system, however, FIG. 14 illustrates the temperature and humidity data inside an exposure chamber for a typical exposure run lasting about 300 minutes. The damp sponges placed in the lower portion of the exposure chamber provide the chamber with a humidity level of around 35%. The exposure chamber air flow rate is maintained at 6 L/min providing good ventilation, and resulting in a stable temperature that matches the temperature of the laboratory ambient air.

REFERENCE LIST

Austin, J. C., P. E. Cleaton-Jones, and E. G. Vieira. 1978. Design and use of an inhalation chamber for air pollution studies in small animals. *Journal of the South African Veterinary Association* 49(3): 235-238.

Baron, P., G. Deye, B. Chen, D. Schwegler-Berry, A. Shedova, and V. Castranova. 2008. Aerosolization of single-walled carbon nanotubes for an inhalation study. *Inhalation toxicology* 20(8) 751-760.

Castranova, V., V. A. Robinson, and D. G. Frazer. 1996. Pulmonary reaction to organic dust exposure. *Environmental Health Perspectives* 104: 41-53.

Chakravarty, P., R. Marches, N. S. Zimmerman, A. D.-E. Swafford, P. Bajaj, I. H. Musselman, P. Pantano, R. K. Draper, and E. S. Vitetta. 2008. Thermal ablation of tumor cells with antibody-functionalized single-walled carbon nanotubes. *PNAS* Jun. 24, 2008; 105(25): 8697-8702.

Frazer, D. G., V. A. Robinson, K. Jayaraman, K. C. Weber, D. S. DeLong, and C. Glance. 1986. Improved operating parameters for the Pitt-3 aerosol generator during resuspension of respirable cotton dust. *Proc. of Tenth Cotton Dust Res. Conf.* R. R. Jacobs and P. J. Wakelyn (eds.) National Cotton Council, Memphis, Tenn. 10:122-125.

Frazer, D. G., V. Robinson, D. S DeLong, D. Rose, J. Tucker, K. C. Weber, S. Olenchock, and K. Jayaraman. 1987. A system for exposing laboratory animals to cotton dust aerosol that is stabilized with feedback control. *Proc. of Eleventh Cotton Dust Res. Conf.* R. R. Jacobs and P. J. Wakelyn (eds.) National Cotton Council, Memphis, Tenn. 11: 74-78.

Han, J. H., E. J. Lee, J. H. Lee, K. P. So, Y. H. Lee, G. N. Bae, S. Lee, J. H. Ji, M. H. Cho, and I. J. Yu. 2008. Monitoring Multiwalled Carbon Nanotube Exposure in Carbon Nanotube Research Facility. *Inhalation Toxicology* 20:741-749.

Liu, A., W. Cai, L. He, N. Nakayama, K. Chen, X. Sun, S. Chen, and H. Dai. 2006. In vivo biodistribution and highly efficient tumor targeting of carbon nanotubes in mice. *Nature Nanotechnology* 2: 47-52.

Maynard, A. D., P. A. Baron, M. Foley, A. A. Shedova, E. R. Eisin, and V. Castranova. 2004. Exposure to carbon nanotube material: aerosol release during the handling of unrefined single-walled carbon nanotube material, *Journal of Toxicology and Environmental Health*, Part A. 67: 87-107.

Maynard A. D., and E. D. Kuempel. 2005. Airborne nanostructured particles and occupational health, *Journal of Nanoparticle Research* 7: 587-614.

McKinney, W., and D. Frazer. 2008. Computer controlled ozone inhalation exposure system. *Inhalation Toxicology* Volume 20, Issue 1: 43-48.

Mitchell, L. A., J. Gao, A. Gigilotti, S. W. Burchiel, and J. D. McDonald. 2007. Pulmonary pathology and systemic immune function following 7, 14, and 30 day exposures to inhaled multi-walled carbon nanotubes (MWCN), *The Toxicologist* 96:1103.

Mitchell, L., J. Gao, R. Vander Wal, A. Gigliotti, S. W. Burchiel, and J. D. McDonald. 2007. Pulmonary and systemic immune response to inhaled multiwalled carbon nanotubes. *Toxicological Sciences* 1000(1): 203-214.

Nise, Norman S. 1995. *Control Systems Engineering*—2$^{nd}$ ed. Addison-Wesley Publishing Company, Menlo Park, Calif.

Oberdörster, G., A. Maynard, K. Donaldson, V. Castranova, J. Fitzpatrick, K. Ausman, J. Carter, B. Karn, W. Kreyling, D. Lai, S. Olin, N. Monteiro-Riviere, D. Warheit, and H. Yang. 2005. Principles for characterizing the potential human health effects from exposure to nanomaterials: elements of a screening strategy. *Particle and Fibre Toxicology* 2:8.

Oberdörster, G., E. Oberdörster, and J. Oberdörster. 2005. Nanotoxicology: An Emerging discipline evolving from studies of ultrafine particles. *Environmental Health Perspectives*, July; 113(7): 823-839.

Oberdorster, G., Z. Sharp, V. Atudorei, A. Elder, R. Gelein, W. Kreyling, and C. Cox. 2004. Translocation of inhaled ultrafine carbon particles to the brain. *Inhalation Toxicology* 16: 437-445.

Phalen, R. F. 1976. Inhalation exposure of animals. *Environmental Health Perspectives* Vol. 16: 17-24.

Wong, B. A., 2007. Inhalation exposure systems: design, methods and operation. *Toxicologic Pathology* 35:3.

Patent documents and publications in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. An aerosol generator comprising:
   an acoustic energy generator;
   an aerosol chamber;
   a first diaphragm having a first side and a second side, and coupled to said aerosol chamber, said first diaphragm being impenetrable to aerosol or substrate;
   said acoustic generator acoustically coupled to said first side of said first diaphragm, said acoustic generator generates acoustic energy of sinusoidally oscillating frequency;
   wherein the atmospheric pressure of a gas atmosphere on said first side or said second side of said first diaphragm is tunable.

2. The generator of claim 1 wherein the atmospheric pressure on said second side of said first diaphragm is higher than the atmospheric pressure on said first side of said first diaphragm.

3. The generator of claim 1 wherein the atmospheric pressure on said second side of said first diaphragm differs from the atmospheric pressure on said first side of said first diaphragm by −0.3 to 0.5 inch-$H_2O$.

4. The generator of claim 1 further comprising an exposure chamber atmospherically coupled to said generator; and
   a nephelometer in contact with said exposure chamber.

5. The generator of claim 1 wherein a focal zone on said first diaphragm is in excess of 2 centimeters.

6. The generator of claim 1 wherein said sinusoidally oscillating frequency is variable above and below a resonant frequency of said first diaphragm, said aerosol chamber, or combinations thereof.

7. The aerosol generator of claim 1 further comprising a second diaphragm, said second diaphragm coupled to said aerosol chamber on a second end opposite said first diaphragm.

8. The aerosol generator of claim 1 further comprising an enclosure surrounding said aerosol chamber and said acoustic generator.

9. The aerosol generator of claim 1 capable of generating aerosols from a substrate of multi-walled carbon nanotube substrate.

10. The generator of claim 1 wherein the atmospheric pressure on said second side of said first diaphragm is 0.1 inch-$H_2O$ higher than the atmospheric pressure on said first side of said first diaphragm.

11. The generator of claim 10 wherein said aerosol concentration is held constant for 30 hours or less using 5 grams of substrate material.

12. The generator of claim 1 wherein an aerosol is produced with a concentration between 0.1 and 15 mg/m$^3$.

13. The generator of claim 12 wherein said concentration is from 5 to 12 mg/m$^3$.

14. The generator of claim 1 further comprising a computer programmed to maintain the concentration of an aerosol generated by said generator to within 20 percent an average or target aerosol concentration for at least 1 hour.

15. The generator of claim 14 wherein said concentration of an aerosol is maintained for between 1 to 25 hours.

16. A process of exposing a subject to an aerosol comprising:
   placing a subject in an exposure chamber, said exposure chamber atmospherically coupled to the generator of claim 1;
   exposing said subject to an aerosol produced by said generator at an aerosol concentration from 0.1 and 15 mg/m$^3$ for an exposure time of at least 1 hour.

17. The process of claim 16 wherein the concentration of said aerosol in said exposure chamber is maintained to within 20 percent of an average or target concentration during said exposure time.

18. The process of claim 16 wherein said exposure chamber includes a nephelometer electrically coupled to a computer, wherein said computer maintains said aerosol concentration constant in response to signal from said nephelometer.

19. A process of generating an aerosol comprising:
   placing an aerosol source on said first diaphragm of the aerosol generator of claim 1; and
   exposing said energy translating surface to an oscillating acoustic energy.

20. The process of claim 19 further comprising separating aerosol particles by elutriation.

21. The process of claim 19 wherein said acoustic energy is oscillated above and below a resonant frequency of said acoustic energy translating surface alone or coupled with an aerosol chamber.

22. The process of claim 19 wherein said oscillating acoustic energy is unfocused.

23. The process of claim 19 wherein said oscillating acoustic energy is less than 1000 Hz.

24. The process of claim 19 wherein said oscillating acoustic energy is less than 40 Hz.

25. The process of claim 19 wherein said aerosol particles are multi-walled carbon nanotubes.

* * * * *